United States Patent
Glausch et al.

(10) Patent No.: US 7,932,241 B2
(45) Date of Patent: Apr. 26, 2011

(54) PHARMACEUTICAL PRODUCTS COMPRISING BISPHOSPHONATES

(75) Inventors: Alexandra Glausch, Weil am Rhein (DE); Rolf Löffler, Freiburg (DE); Juergen Sigg, Loerrach (DE)

(73) Assignee: Novartis AG, Basel (CH)

( * ) Notice: Subject to any disclaimer, the term of this patent is extended or adjusted under 35 U.S.C. 154(b) by 1236 days.

(21) Appl. No.: 10/570,339

(22) PCT Filed: Sep. 17, 2004

(86) PCT No.: PCT/EP2004/010470
§ 371 (c)(1),
(2), (4) Date: Aug. 11, 2006

(87) PCT Pub. No.: WO2005/025551
PCT Pub. Date: Mar. 24, 2005

(65) Prior Publication Data
US 2007/0015736 A1    Jan. 18, 2007

Related U.S. Application Data

(60) Provisional application No. 60/504,402, filed on Sep. 18, 2003.

(51) Int. Cl.
*A61K 31/66* (2006.01)

(52) U.S. Cl. ........................................................ 514/108
(58) Field of Classification Search ................... 514/108
See application file for complete search history.

(56) References Cited

FOREIGN PATENT DOCUMENTS

| JP | A-08-92102 | 4/1996 |
|---|---|---|
| WO | 02/22136 | 3/2002 |
| WO | 02/087592 | 11/2002 |
| WO | 02/089768 | 11/2002 |
| WO | WO 2005/025551 | 3/2005 |

OTHER PUBLICATIONS

Nakamura et al., "Failure of Stability Prediction for Minodronic Acid Injectable by Accelerated Stability Testing", International Journal of Pharmaceutics, vol. 241, No. 1, pp. 65-71 (2002).

Tchiakpe et al., "Stedim 6 and Clearflex, Two New Multilayer Materials for Infusion Containsers. Comparative Study of their Compatibility with Five Drugs Versus Glass Flasks and Polyvinyl Chloride Bags", Journal of Biomaterials Science Polymer Edition, vol. 7, No. 3, pp. 199-206 (1995).

Okuda et al., "Stems used in drug names: for the better understanding of pharmacological actions of drugs". Pharm. Tech. Japan, vol. 24, No. 13, (2008), pp. 2687-2693.

*Primary Examiner* — Raymond J Henley, III
(74) *Attorney, Agent, or Firm* — Leslie Fischer

(57) ABSTRACT

A pharmaceutical product comprises a container containing a bisphosphonate solution, in which at least the internal surface of the container comprises a plastic material and in which the container is heat sterilisable, and which is in the form of a ready to use infusion solution, for administration of the bisphosphonate to a patient in need of bisphosphonate treatment.

30 Claims, No Drawings

PHARMACEUTICAL PRODUCTS COMPRISING BISPHOSPHONATES

This application is a National Stage entry of International Application PCT/EP2004/010470, filed Sep. 17, 2004, which claims benefit of U.S. Provisional Application No. 60/504,402, filed Sep. 18, 2003, the contents of which in their entirety are herein incorporated by reference.

This invention relates to pharmaceutical products and processes for their production, in particular to pharmaceutical products comprising bisphosphonates and to processes for producing such bisphosphonate products.

Bisphosphonates are widely used to inhibit osteoclast activity in a variety of both benign and malignant diseases which involve excessive or inappropriate bone resorption. These pyrophosphate analogs not only reduce the occurrence of skeletal related events but they also provide patients with clinical benefit and improve survival. Bisphosphonates are able to prevent bone resorption in vivo; the therapeutic efficacy of bisphosphonates has been demonstrated in the treatment of osteoporosis, osteopenia, Paget's disease of bone, tumour-induced hypercalcemia (TIH) and, more recently, bone metastases (BM) and multiple myeloma (MM) (for review see Fleisch H 1997 Bisphosphonates clinical. In Bisphosphonates in Bone Disease. From the Laboratory to the Patient. Eds: The Parthenon Publishing Group, New York/London pp 68-163).

Customary bisphosphonate dosage forms, e.g. for the treatment of TIH, BM and MM, are intravenous infusion solutions. However, bisphosphonates solutions, although intrinsically stable, react with di-and polyvalent cations, especially calcium, barium, magnesium, aluminium, boron, and silicon present in glass to form insoluble precipitates giving rise to turbidity and possible loss of potency, neither of which can be tolerated in a pharmaceutical product. Further such precipitates may lead to blockage of blood vessels and thus could cause a thrombosis as serious complication of the medication. Thus long term storage of bisphosphonate solution formulations in standard glass vials, even of hydrolytic resistance class I quality is not possible. Also such solution in glass products cannot be terminally moist heat sterilized, and must be aseptically filled, because the leaching of cations is accelerated under the elevated temperature conditions of moist heat sterilization. It has been shown that at pH values acceptable for parenteral delivery, significant amounts of ions are leached out of commercially available glass containers (Farm. Vestnik. Vol 54, p. 331 (2003)). Consequently, for short term storage of solution in glass products it would be necessary to aseptically fill the solutions, although in view of their high chemical stability heat sterilisation of bisphosphonate solutions is inherently possible. Such aseptic filling does not comply with the currently accepted processing norms, as outlined in the document no. CPMP/QWP/054/98 corr., "Decision trees for the selection of sterilisation methods" issued by the European Agency for the Evaluation of Medicinal Products (EMEA). The same document also states that "the use of an inappropriate heat-labile packaging material cannot be in itself the sole reason for adoption of aseptic processing".

Consequently bisphosphonate products for iv infusion are typically provided in the form of solid lyophilisates, which do not show microbial growth promoting properties when compared with unpreserved bisphosphonate solutions at physiologically acceptable pHs. The lyophilisates are made up into the infusion solution with water for injection or other aqueous solvents shortly before use, e.g. Aredia® and Zometa®. In view of the low solubility of the precipitates formed with divalent and polyvalent cations, even the low levels of alkaline earth metal impurities present in all commercially available grades of sodium chloride and saline solutions could result in formation of such precipitates when diluting concentrated bisphosphonic acid solutions.

Recently it has been proposed (WO 02/22136, F. H. Faulding & Co Ltd.) to provide a pharmaceutical product comprising a container containing a diphosphonate in solution, wherein the solution: (a) has a pH of between 5 and 8; and (b) is free of organic buffer and polyethylene glycol and wherein the container is a glass container in which the surface in contact with the solution has been pre-treated to protect against leaching of impurities from the glass by the solution or wherein the container consists of at least one component manufactured from a non-glass material, such as polyethylene, polypropylene and polymethylpentene. However, WO 02/22136 does not include any teaching as to how, when or if the product is sterilised. Further this reference does not give guidance on how to keep the pH value stable over storage time if highly potent low dosed bisphosphonates as e.g. zoledronic acid is formulated.

It has now been found that bisphosphonate solutions may be formulated for long term storage in containers comprising polymeric materials which containers do not chemically interact with the bisphosphonate solution and which may be conveniently terminally sterilised.

Accordingly the present invention provides a ready-to-use bisphosphonate pharmaceutical product comprising a container containing a bisphosphonate solution, in which at least the internal surface of the container comprises a plastic material and in which the container is heat sterilisable.

The products of the present invention are advantageously solution products for parenteral administration which do not require reconstitution of a lyophilisate prior to use. Conveniently also the product may be heat sterilised in situ in the container during production, preferably terminally moist heat sterilised (e.g. by steam thus advantageously obtaining a Sterility Assurance Level of at least $10^{-6}$). Additionally, these ready-to-use solutions do not require dilution prior to use.

The products of the invention may be administered orally, transdermally, or by injection, e.g. subcutaneously, arterially or intravenously. Most preferably the products of the invention are administered by intravenous infusion.

The products of the invention comprise solutions which are ready to use, in which the bisphosphonate is present at a concentration suitable for direct administration without dilution and as such are referred to as "ready to use solutions".

Preferably the ready to use solution product is in the form of a unit dose ready to use solution, i.e. contains sufficient bisphosphonate for a single dose treatment. Such unit dose ready to use solution products for infusion typically have a volume in the range from about 20 up to about 500 ml, usually from about 50 to about 250 ml, preferably about 100 ml (wherein such volumes may additionally include up to about 20 ml, e.g. preferably about 2 ml, overfill to accommodate for liquid remaining in the container when the ready to use solution is infused to a patient.).

Such ready to use solutions advantageously are brought to a physiologically acceptable pH value with bases. It has been found that with organic bases that have cation complexing properties slight hazes due to precipitates of the drug substance with cationic impurities of the excipients used can be avoided. It further has been found that compared to strong inorganic bases as sodium hydroxide, a slight buffering system is formed in situ with the bisphosphonate itself which enables more easily adjustment of the desired pH-value and ensures optimal stability of the pH value over the whole storage time. The pH of the solution is preferably in the region from about pH 4.5 up to about pH 8, more preferably in the range from about pH 5.5 up to about pH 7.5, e.g. about pH 6.5 or about pH 6.8 or about pH 7.2. Examples of suitable organic bases include the sodium or potassium salts of organic acids as acetic acid, citric acid, lactic acid, glutamic acid, tartaric acid, fumaric acid, maleic acid, or malic acid. Furthermore, basic forms of amino acids may be used, e.g. histidine or arginine. Examples of suitable anorganic bases are sodium or potassium phosphate, sodium hydrogen carbonate or sodium hydroxide. Also mixtures of the above bases, or mixtures of the bases with their corresponding acids may be used. For example, the formulation may comprise a base, e.g. sodium citrate, with an acid, e.g. hydrochloric acid. Preferably the base is a sodium or potassium salt. When using potassium salts, the physiological tolerability of such formulations however have to be carefully assessed, and it is recommended not to exceed the physiological concentration of potassium in blood serum which is approx. 4 milli-moles per litre.

Such ready to use solutions may also typically comprise an isotonising agent. Preferably the tonicity of the solution is in the range from about 250 mOsm/kg up to about 400 mOsm/kg, more preferably from about 260 mOsm/kg up to about 350 mOsm/kg, e.g. about 300 mOsm/kg. Examples of suitable isotonising agents are: glycerol, polyethylene glycol, propylene glycol, ethanol, cyclodextrins, amino acids, sugars and sugar alcohols including: Glucose, fructose, mannose, mannitol, saccharose, lactose, trehalose, maltose, sorbitol, sodium chloride, sodium nitrate, potassium chloride, urea, ammonium chloride. Preferably the isotonising agent is a non-ionic isotonising agent, more preferably a sugar, ester, alcohol or polyol. Particularly preferred isotonising agents for use in the solution pre-concentrate are mannitol, 1,2 propylene glycol, glycerol and sorbitol, of which mannitol is particularly preferred.

It has been found in accordance with the present invention that the use of non-ionic isotonising agents permits easy and reliable analysis, e.g. by ion chromatography, capillary electrophoresis, and high performance liquid chromatography (HPLC). It has been found, that with reversed phase HPLC using an ion pair reagent (e.g. tetrahexylammonium hydrogen sulfate) and a complexation reagent (e.g. ethylendiamintetraacetic acid, EDTA) and the UV detection mode a very low concentration of the bisphophonate and especially of potential by-and degradation products can be reliably determined. It is highly desirable to be able to detect such potential by-and degradation products at the low concentrations at which they are present in ready to use solution products. No derivatization step is necessary. For the ready to use solution product of the present invention a concentrations of 0.04 µg/ml can be reliably quantified. This corresponds to 0.1% related to the declared dose, which is the reporting limit, which has to be achieved in order to comply with international regulatory guidelines.

In contrast, if one of the customary ionic isotonising agents, e.g. sodium chloride, is used, these interfere with the chromatographic measurements to an extent that potential by-and degradation products cannot be reliably quantified.

Thus in particular embodiments the invention includes product as defined above, in which the isotonising agent is non-ionic:
  i) and in which the product is analysable with a limit of quantitation for the bisphophonate and its by-and degradation products of at least 0.1% related to the declared dose, preferably without applying a derivatization step, and
  ii) A product as defined above, which is analysable by reversed phase chromatography with a complexation agent, e.g. EDTA, for determination of the bisphophonate and its by-and degradation products with a limit of quantitation of at least 0.1% related to the declared dose, preferably without applying a derivatization step.

Thus in a further preferred embodiment the invention provides a pharmaceutical product comprising a container containing a bisphosphonate solution in the form of a ready to use solution, comprising a) a unit dose of a bisphosphonate,
  b) an organic base, and
  c) a non-ionic isotonising agent
  in which at least the internal surface of the container comprises a transparent plastic material and in which the filled container is terminally heat sterilisable.

Ready to use solution products may be provided in infusion bags; for instance as customarily used for infusion of other therapeutic infusion products, e.g. plastic infusion bags made of polyvinyl chloride, polyolefine copolymers, a Cryovac® M312 foil (Sealed Air Corporation), Baxter Intravia®, and B.Braun PAB (polypropylene with 10% of styrene ethylene-butylenes styrene (SEBS) thermoplastic elastomer) or similar infusion bags.

The container for the product of the invention may comprise a glass container having a transparent plastic inner lining. Preferably, however, the container is made of plastic material and does not comprise a glass outer shell. Examples of plastic materials which may be used include: polysulfone, polycarbonate, polypropylene, polyethylene (LDPE or HDPE), ethylene/propylene copolymers, polyolefines, acrylic-imide copolymers, PVC, polyester (e.g. PET, PEN and the like), Teflon, Nylon, acetal (Delrin), polymethylpentene, PVDC, ethylvinylacetate, AN-copolymer etc. The plastic material used for either type of container is preferably a transparent plastic material, i.e. it is translucent and permits visual inspection of the contents.

Furthermore the plastic material used is a plastic which is capable of withstanding heat sterilisation in the filled and unfilled state, preferably moist heat sterilisation e.g. steam sterilisation or superheated water showering sterilisation, at a temperature of at least about 110° C. to about 130° C. or higher, e.g. at a temperature of at least 121° C., e.g. at 121-124° C.

Particularly preferred plastic materials for the container are transparent cycloolefinic polymers such as Daikyo CZ resin, thermoplastic olefin polymers of amorphous structure (e.g. TOPAS, manufactured by Ticona). Most preferred are Daikyo CZ resin and similar cycloolefinic polymers.

Ready to use products may be provided in plastic or plastic-coated bottles having a volume from about 20 ml up to about 500 ml, e.g. about 100 ml.

Bisphosphonate solutions may also be administered by slow intraveneous injection of a more concentrated form, e.g. with a concentration in the range from about 0.01 to about 0.5, more usually from about 0.05 up to about 0.2 mg bisphosphonate/ml. For this purpose the product may also be filled into prefillable syringes that can be terminally moist heat sterilized, e.g. in syringes made of Daikyo CZ resin or similar or of thermoplastic olefin polymers of amorphous structure (e.g. as sold by Schott under the trade name Schott Top Pac or similar)

Commercially available plastic container materials like the Daikyo CZ resin further have a thermal deformation temperature according to ASTM D648 of 123° C., which would narrow down the acceptable sterilization temperature to at most 123° C. It has now been found that sterilization even at significantly higher temperatures of e.g. up to 130° C., lead neither to measurable deformations of the container nor to impaired container closure integrity.

Preferably the bisphosphonates for use in the invention are the nitrogen containing bisphosphonates, including those having side chains which contain amino groups or especially those having side chains containing nitrogen-containing heterocycles, most especially containing aromatic nitrogen-containing heterocycles.

Examples of suitable bisphosphonates for use in the invention may include the following compounds or a pharmaceutically acceptable salt thereof: 3-amino-1-hydroxypropane-1,1-diphosphonic acid (pamidronic acid), e.g. pamidronate (APD); 3-(N,N-dimethylamino)-1-hydroxypropane-1,1-diphosphonic acid, e.g. dimethyl-APD; 4-amino-1-hydroxybutane-1,1-diphosphonic acid (alendronic acid), e.g. alendronate; 1-hydroxy-ethidene-bisphosphonic acid, e.g. etidronate; 1-hydroxy-3-(methylpentylamino)-propylidene-bisphosphonic acid, ibandronic acid, e.g. ibandronate; 6-amino-1-hydroxyhexane-1,1-diphosphonic acid, e.g. amino-hexyl-BP; 3-(N-methyl-N-n-pentylamino)-1-hydroxypropane-1,1-diphosphonic acid, e.g. methyl-pentyl-APD (=BM 21.0955); 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate, including N-methyl pyridinium salts thereof, for example N-methylpyridinium iodides such as NE-10244 or NE-10446; 1-(4-chlorophenylthio)methane-1,1-diphosphonic acid (tiludronic acid), e.g. tiludronate; 3-[N-(2-phenylthioethyl)-N-methylamino]-1-hydroxypropane-1,1-diphosphonic acid; 1-hydroxy-3-(pyrrolidin-1-yl)propane-1,1-diphosphonic acid, e.g. EB 1053 (Leo); 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U-81581 (Upjohn); 1-hydroxy-2-(imidazo[1,2-a]pyridin-3-yl)ethane-1,1-diphosphonic acid, e.g. YM 529; and 1,1-dichloromethane-1,1-diphosphonic acid (clodronic acid), e.g. clodronate.

A particularly preferred bisphosphonate for use in the invention comprises a compound of Formula I

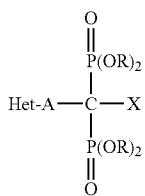

wherein
Het is an imidazole, oxazole, isoxazole, oxadiazole, thiazole, thiadiazole, pyridine, 1,2,3-triazole, 1,2,4-triazole or benzimidazole radical, which is optionally substituted by alkyl, alkoxy, halogen, hydroxyl, carboxyl, an amino group optionally substituted by alkyl or alkanoyl radicals or a benzyl radical optionally substituted by alkyl, nitro, amino or aminoalkyl;
A is a straight-chained or branched, saturated or unsaturated hydrocarbon moiety containing from 1 to 8 carbon atoms;
X is a hydrogen atom, optionally substituted by alkanoyl, or an amino group optionally substituted by alkyl or alkanoyl radicals, and
R is a hydrogen atom or an alkyl radical,
and the pharmacologically acceptable salts thereof.

Examples of particularly preferred bisphophonates for use in the invention are:
2-(1-Methylimidazol-2-yl)-1-hydroxyethane-1,1-diphosphonic acid;
2-(1-Benzylimidazol-2-yl)-1-hydroxyethane-1,1-diphosphonic acid;
2-(1-Methylimidazol-4-yl)-1-hydroxyethane-1,1-diphosphonic acid;
1-Amino-2-(1-methylimidazol-4-yl)ethane-1,1-diphosphonic acid;
1-Amino-2-(1-benzylimidazol-4-yl)ethane-1,1-diphosphonic acid;
2-(1-Methylimidazol-2-yl)ethane-1,1-diphosphonic acid;
2-(1-Benzylimidazol-2-yl)ethane-1,1-diphosphonic acid;
2-(Imidazol-1-yl)-1-hydroxyethane-1,1-diphosphonic acid;
2-(Imidazol-1-yl)ethane-1,1-diphosphonic acid;
2-(4H-1,2,4-triazol-4-yl)-1-hydroxyethane-1,1-diphosphonic acid;
2-(Thiazol-2-yl)ethane-1,1-diphosphonic acid;
2-(Imidazol-2-yl)ethane-1,1-diphosphonic acid;
2-(2-Methylimidazol-4(5)-yl)ethane-1,1-diphosphonic acid;
2-(2-Phenylimidazol-4(5)-yl)ethane-1,1-diphosphonic acid;
2-(4,5-Dimethylimidazol-1-yl)-1-hydroxyethane-1,1-diphosphonic acid, and
2-(2-Methylimidazol-4(5)-yl)-1-hydroxyethane-1,1-diphosphonic acid,
and pharmacologically acceptable salts thereof.

More preferred bisphosphonates for use in the invention are Disodium-3-amino-1-hydroxy-propylidene-1,1-bisphosphonate pentahydrate (pamidronic acid) and 2-(imidazol-1yl)-1-hydroxyethane-1,1-diphosphonic acid (zoledronic acid) or pharmacologically acceptable salts thereof.

The most preferred bisphosphonate for use in the invention is 2-(imidazol-1yl)-1-hydroxyethane-1,1-diphosphonic acid (zoledronic acid) or a pharmacologically acceptable salt thereof.

Particularly preferred ready to use products are in unit dose form and comprise from 2 to 10 mg of zoledronic acid or a pharmaceutically acceptable salt thereof. Most preferably the zoledronate unit dose product comprises an equivalent to 4 mg or 5 mg of anhydrous zoledronic acid, in particular as hereinafter described in the Examples.

Pharmacologically acceptable salts are preferably salts with bases, conveniently metal salts derived from groups Ia, Ib, IIa and IIb of the Periodic Table of the Elements, including alkali metal salts, e.g. potassium and especially sodium salts, and also ammonium salts with ammonia or organic amines.

Especially preferred pharmaceutically acceptable salts are those where one, two, three or four, in particular two or three, of the acidic hydrogens of the bisphosphonic acid are replaced by a pharmaceutically acceptable cation, in particular sodium, potassium or ammonium, in first instance sodium.

A very preferred group of pharmaceutically acceptable salts is characterized by having at least one acidic hydrogen and one pharmaceutically acceptable cation, especially sodium, in each of the phosphonic acid groups.

All the bisphosphonic acid derivatives mentioned above are well known from the literature. This includes their manufacture (see e.g. EP-A-513760, pp. 13-48). For example, 3-amino-1-hydroxypropane-1,1-diphosphonic acid is prepared as described e.g. in U.S. Pat. No. 3,962,432 as well as the disodium salt as in U.S. Pat. Nos. 4,639,338 and 4,711,880, and 1-hydroxy-2-(imidazol-1-yl)ethane-1,1-diphosphonic acid is prepared as described e.g. in U.S. Pat. No. 4,939,130. See also U.S. Pat. Nos. 4,777,163 and 4,687,767 and EP 0 275 821 B.

The invention also includes processes for the production of the solution products of the invention, which processes typically comprise a terminal heat sterilization step.

Accordingly in a further aspect the invention comprises a process for the production of a pharmaceutical product comprising a container containing a bisphosphonate solution, in which a bisphosphonate solution is provided within a container in which at least the internal surface of the container comprises a transparent plastic material and in which the container containing the bisphosphonate solution is terminally heat sterilised.

Thus the container containing the bisphosphonate solution is heat sterilized, preferably moist heat sterilised e.g. by saturated steam, steam/air mixtures or superheated water showering sterilisation, at a temperature of at least about 110° C. to about 130° C. or higher, e.g. at a temperature of at least 121° C. or higher, e.g. preferably at about 121-124° C. The effective sterilization time depends on the D-value of test spores in the solution and should be dimensioned that an overall SAL of at least $10^{-6}$, preferably of at least $10^{-12}$ is obtained. The effective sterilization time (dwell time) may be from about 15 minutes up to about 3 hours, conveniently from about 15 minutes to about 2 hours, e.g. preferably about 30 min. Advantageously the heat sterilisation is terminal heat sterilisation, i.e. heat sterilisation which is carried out near to or at completion of the production process, after filling of the container with the bisphosphonate solution and preferably after closure of the container, e.g. with a suitable cap, stopper or other closure. Conveniently standard production equipment for processing of glass vials may be used.

Suitable rubber stoppers are those which show only negligible leaching of metal ions like calcium, magnesium, zinc or silica when contacted with aqueous solutions, e.g. bisphosphonate solutions. Preferred stoppers have a low ash content and are coated on the product side with an impermeable and inert barrier, e.g. made of ETFE, Teflon or fluorinated elastomers. Suitable stoppers are e.g. Daikyo D-777-1, Daikyo D-777-3, Daikyo D-713, Daikyo D-21-7S, all coated on the product side with an ETFE layer, or Helvoet FM259/0 coated with a layer of a fluoropolymer (e.g. the Helvoet proprietary material Omniflex or Omniflex plus).

The ready to use bisphosphonate solution may be prepared in bulk and delivered to the containers; for instance, using the customary art procedures. The bulk bisphosphonate solution may be in the form of a solution of the free bisphosphonic acid, e.g. zoledronic acid, or in the form of a salt thereof, e.g. the sodium salt. Bulk bisphosphonate salt solutions may be prepared by dissolving the salt in aqueous media, or may be prepared in situ in solution by reaction of a dispersion of the free bisphophonic acid with a base, e.g. neutralisation of the acid with sodium hydroxide to give the mono sodium salt, disodium salt, trisodium salt or tetra sodium salt as desired, e.g. disodium pamidronate or disodium zoledronate.

According to GMP requirements, all container material used for parenteral products are to be subjected to a depyrogenization process ensuring an endotoxin reduction of at least 3 log units. Heat depyrogenisation is customarily used for glass vials. However, plastic vials generally cannot be processed on standard pharmaceutical sterile drug product filling lines, as such containers would not withstand the thermal stress applied in the heat depyrogenization tunnel. Therefore, plastic vials are usually processed without the necessary cleaning and depyrogenization steps, thus bearing the risk of contamination of the parenteral drug product with foreign matter present in the vials as well as with Endotoxins that may be dissolved from the vial material surface. Surprisingly it has been found in accordance with the present invention that some plastic containers can be processed on standard filling lines for glass vials, and that provided the washing process is suitably adjusted an endotoxin reduction by the factor of at least 1000 can be reproducibly obtained.

Thus in addition to the sterilisation step, the containers, in particular the plastic containers, may be depyrogenised prior to filling with bisphosphonate solution. We have found that washing of the plastic vials with water under pressure gives satisfactory depyrogenisation, e.g. reduction in endotoxin concentration by a factor of at least 1000 or more, e.g. about 16000-100000. Such a depyrogenisation step is preferably included within the production processes of the invention.

Alternatively endotoxin-free or substantially endotoxin-free plastic containers may be obtained from a supplier and such containers used without need for depyrogenisation.

Furthermore the invention includes processes for preparation of the products of the invention as defined above in which reversed phase chromatography with a complexation agent, e.g. EDTA, is used for determination of the bisphophonate and its by-and degradation products, advantageously with a limit of quantitation of at least 0.1% related to the declared dose, preferably without applying a derivatization step.

The particular mode of administration and the dosage for the products of the invention may be selected by the attending physician talking into account the particulars of the patient, especially age, weight, life style, activity level, hormonal status (e.g. post-menopausal) and bone mineral density as appropriate. Most preferably, however, the bisphosphonate is administered intravenously.

Normally the dosage is such that a single dose of the bisphosphonate active ingredient from 0.002-20.0 mg/kg, especially 0.01-10.0 mg/kg, is administered to a warm-blooded animal weighing approximately 75 kg. If desired, this dose may also be taken in several, optionally equal, partial doses.

"mg/kg" means mg drug per kg body weight of the mammal—including man—to be treated.

Preferably, the bisphosphonates are administered in doses which are in the same order of magnitude as those used in the treatment of the diseases classically treated with bisphosphonic acid derivatives, such as Paget's disease, tumour-induced hypercalcemia or osteoporosis. In other words, preferably the bisphosphonic acid derivatives are administered in doses which would likewise be therapeutically effective in the treatment of Paget's disease, tumour-induced hypercalcaemia or osteoporosis, i.e. preferably they are administered in doses which would likewise effectively inhibit bone resorption.

The following Examples illustrate the invention described hereinbefore.

EXAMPLES

Example 1

Zoledronic Acid 4 mg/100 mL

| Ingredient | Amount [kg] per 1000 L |
| --- | --- |
| Zoledronic acid monohydrate Corresponding to 0.0400 kg zoledronic acid anhydrous | 0.04264 kg |
| Mannitol | 51.00 kg |
| Sodium citrate | 0.240 kg |
| Water for injection | Up to 1'015 kg = 1000 L |

Approx. 85-95% of the total amount of water for injection is filled into a stainless steel compounding vessel. The excipients mannitol and sodium citrate are added and dissolved under stirring. The drug substance zoledronic acid is added and dissolved under stirring. The preparation is adjusted to the final weight with water for injection. The amount of sodium citrate neutralizes the zoledronic acid to a pH value of 6.5. The bulk solution is passed to the filling line and filtered in-line through a filter of 0.2 μm pore size. Washed and dried 100 mL Daikyo CZ plastic vials are filled with 102.0 ml of bulk solution. Sterilized Helvoet FM259/0 Omniflex plus coated stoppers are inserted into the vials, and the stoppered vials are sealed with aluminium caps. The vials are sterilized with moist heat to obtain a Sterility Assurance Level of $10^{-12}$, i.e. at 121-123° C. for 30 minutes (effective dwell time).

The product is stable and does not show any sign for degradation eve under severe stress conditions of 50° C./75% RH and 40° C./75% RH.

| Test | Start | 40° C./ 75% rel. humidity 3 months | 50° C./ 75% rel. humidity 1 month |
|---|---|---|---|
| Assay | 99.5% | 101.4% | 98.8% |
| Degradation products, sum | <0.1% | <0.1% | <0.1% |
| pH-value | 6.7 | 6.6 | 6.6 |
| Appearance | clear, colorless particle-free solution | clear, colorless particle-free solution | clear, colorless particle-free solution |
| Extractables | <0.05 µg/mL | <0.05 µg/mL | <0.05 µg/mL |

Example 2

Zoledronic Acid 5 mg/100 mL

| Ingredient | Amount [kg] per 1000 L |
|---|---|
| Zoledronic acid monohydrate Corresponding to 0.0500 kg zoledronic acid anhydrous | 0.0533 kg |
| Mannitol | 49.50 kg |
| Sodium citrate | 0.300 kg |
| Water for injection | Up to 1'014.5 kg = 1000 L |

Approx. 85-95% of the total amount of water for injection is filled into a stainless steel compounding vessel. The excipients mannitol and sodium citrate are added and dissolved under stirring. The drug substance zoledronic acid is added and dissolved under stirring. The preparation is adjusted to the final weight with water for injection. The amount of sodium citrate neutralizes the zoledronic acid to a pH value of 6.5. The bulk solution is passed to the filling line and filtered in-line through a filter of 0.2 µm pore size. Washed and dried 100 mL Daikyo CZ plastic vials are filled with 102.0 ml of bulk solution. Sterilized Helvoet FM259/0 Omniflex plus coated stoppers are inserted into the vials, and the stoppered vials are sealed with aluminium caps. The vials are sterilized with moist heat to obtain a Sterility Assurance Level of $10^{-12}$, i.e. at 121-123° C. for 30 minutes (effective dwell time).

The product is stable and does not show any sign for degradation eve under severe stress conditions of 50° C./75% RH and 40° C./75% RH.

| Test | Start | 30° C./70% rel. humidity 12 months | 40° C./75% rel humidity inverse storage 6 months |
|---|---|---|---|
| Assay | 99.8% | 100.0% | 99.9% |
| Degradation products, sum | <0.1% | <0.1% | <0.1% |
| pH-value | 6.6 | 6.6 | 6.4 |
| Particulate matter (USP) ≧10 µm | 10 | 10 | 5 |
| ≧25 µm | 0 | 0 | 0 |
| Appearance | clear, colorless solution | clear, colorless solution | clear, colorless solution |
| Extractables | <0.05 µg/mL | <0.05 µg/mL | <0.05 µg/mL |

-continued

| Test | Start | 30° C./70% rel. humidity 12 months | 40° C./75% rel humidity inverse storage 6 months |
|---|---|---|---|
| Heavy Metals | | | |
| Ca | <50 µg/L | <50 µg/L | <50 µg/L |
| Mg | <50 µg/L | <50 µg/L | <50 µg/L |
| Al | <100 µg/kg | <100 µg/kg | <100 µg/kg |
| Cd | <100 µg/kg | <100 µg/kg | <100 µg/kg |
| Cr | <100 µg/kg | <100 µg/kg | <100 µg/kg |
| Cu | <100 µg/kg | <100 µg/kg | <100 µg/kg |
| Fe | <100 µg/kg | <100 µg/kg | <100 µg/kg |
| Ti | <100 µg/kg | <100 µg/kg | <100 µg/kg |
| Zn | <100 µg/kg | <100 µg/kg | <100 µg/kg |

Example 3

Adjustment of pH Value in Zoledronic Acid Formulations with Different Bases 533.1 mg of zoledronic acid monohydrate (equivalent to 500 mg of zoledronic acid) and 480.0 g of mannitol are added to 7520 g of water for injection and stirred until a clear solution with a total weight of 8000 g is obtained. Each 800 g of this solution (equivalent to 50 mg of zoledronic acid) are titrated with (a) a solution of 0.500 g/100 mL trisodium citrate dihydrate in water for injection
(b) a solution of 0.500 g/100 mL anhydrous sodium acetate in water for injection
(c) a solution of 0.500 g/100 mL disodium tartrate dihydrate in water for injection
(d) a solution of 0.500 g/100 mL trisodium phosphate hexahydrate in water for injection
(e) a solution of 0.400 g/100 mL sodium hydroxide in water for injection The pH value after each addition of 200 µL of base solution is recorded potentiometrically. The data show that due to the pKa values of zoledronic acid of 5.9 and 8.28, a steep increase of the pH value in the physiologically most preferred pH range of pH 6 to 7.5 is seen when using sodium hydroxide as base. Compared to that with sodium phosphate and sodium citrate the dissociation of the zoledronic acid acidic groups is slightly buffered, and therefore the desired pH value of usually pH 6.0-7.5 easily can be adjusted.

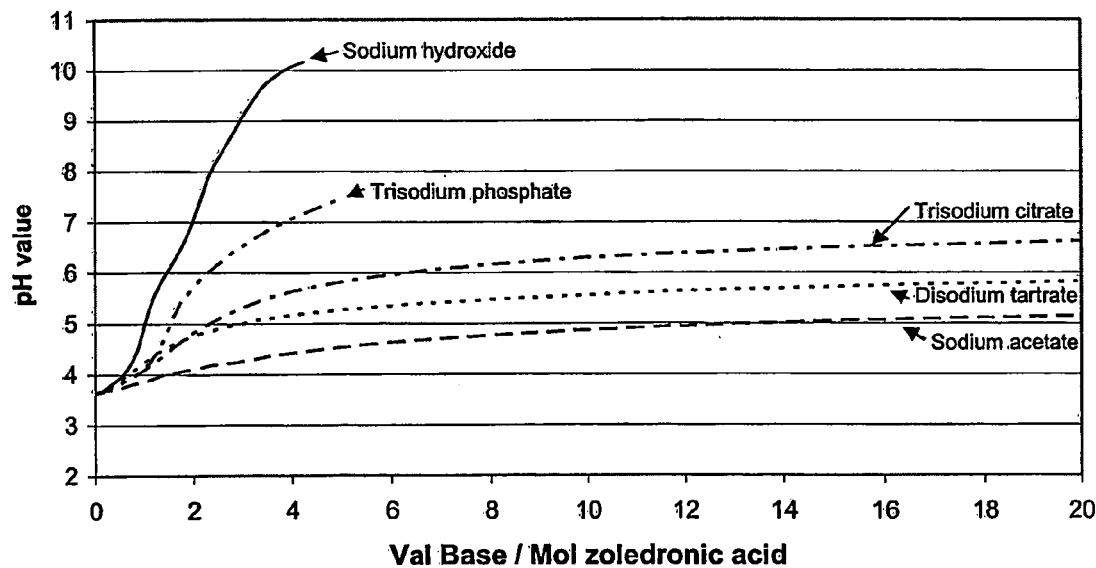

Example 4

Zoledronic Acid 5 mg/100 mL Formulated with
Trisodium Citrate at Different pH Values

| Ingredient | Formulation 4A: pH 6.0 | Formulation 4B: pH 6.5 | Formulation 4C: pH 7.0 |
|---|---|---|---|
| Zoledronic acid monohydrate Corresponding to 50 mg zoledronic acid anhydrous | 53.3 mg | 53.3 mg | 53.3 mg |
| Mannitol | 50.0 g | 49.5 g | 47.0 g |
| Trisodium citrate dihydrate | 0.115 g | 0.300 g | 1.00 g |
| Water for injection | Up to 1.00 L | Up to 1.00 L | Up to 1.00 L |

Example 5

Zoledronic Acid 5 mg/100 mL Formulated with
Trisodium Phosphate at Different pH Values

| Ingredient | Formulation 5A: pH 6.0 | Formulation 5B: pH 6.5 | Formulation 5C: pH 7.0 | Formulation 5D: pH 7.5 |
|---|---|---|---|---|
| Zoledronic acid monohydrate Corresponding to 50 mg zoledronic acid anhydrous | 53.3 mg | 53.3 mg | 53.3 mg | 53.3 mg |
| Mannitol | 50.0 g | 50.0 g | 50.0 g | 50.0 g |
| Trisodium phosphate hexahydrate | 0.038 g | 0.050 g | 0.065 g | 0.085 g |
| Water for injection | Up to 1.00 L | Up to 1.00 L | Up to 1.00 L | Up to 1.00 L |

Example 6

Zoledronic Acid 5 mg/100 mL Formulated with
Sodium Acetate at Different pH Values

| Ingredient | Formulation 6A: pH 5.5 | Formulation 6B: pH 6.0 |
|---|---|---|
| Zoledronic acid monohydrate Corresponding to 50 mg zoledronic acid anhydrous | 53.3 mg | 53.3 mg |
| Mannitol | 49.5 g | 49.0 g |
| Sodium acetate anhydrous | 0.125 g | 0.500 g |
| Water for injection | Up to 1.00 L | Up to 1.00 L |

Example 7

Zoledronic Acid 4 mL/100 mL

| Ingredient | Amount [kg] per 1000 L |
|---|---|
| Zoledronic acid monohydrate Corresponding to 0.0400 kg zoledronic acid anhydrous | 0.04264 kg |
| Mannitol | 51.00 kg |
| Sodium citrate | 0.240 kg |
| Water for injection | Up to 1'015 kg = 1000 L |

Approx. 85-95% of the total amount of water for injection are filled into a stainless steel compounding vessel. The excipients mannitol and sodium citrate are added and dissolved under stirring. The drug substance zoledronic acid is added and dissolved under stirring. The preparation is adjusted to the final weight with water for injection. The bulk solution is passed to the filling line and filter in-line through a filter of 0.2 μm pore size. Empty plastic infusion bags made of a Cryovac® M312 foil (Sealed Air Corporation), Baxter Intravia®, and B.Braun PAB® (polypropylene based foil) are filled with each 102.0 ml of bulk solution. The bags are hermetically sealed. The bags are sterilized with moist heat under a supportive pressure of at least 100 mbar above the water vapour pressure at the chamber temperature (superheated water showering or steam/air mixture) to obtain a Sterility Assurance Level of $10^{-12}$, i.e. at 121-123° C. for 30 minutes (effective dwell time).

Example 8

Zoledronic Acid 5 mg/100 mL

| Ingredient | Amount [g] per 1 L |
|---|---|
| Zoledronic acid monohydrate Corresponding to 0.0500 g zoledronic acid anhydrous | 0.0533 g |
| Sorbitol crystalline | 50.0 g |
| Sodium citrate | 0.300 g |
| Water for injection | Up to 1.00 L |

Approx. 800 g of water for injection are filled into the compounding vessel. The excipients Sorbitol and sodium citrate are added and dissolved under stirring. The drug substance zoledronic acid is added and dissolved under stirring.

The preparation is adjusted to the final volume with water for injection. The solution is filtered into the vials through a filter of 0.2 μm pore size. Washed and dried Daikyo CZ plastic vials are filled with the bulk solution. Sterilized Helvoet FM259/0 Omniflex plus coated stoppers are inserted into the vials, and the stoppered vials are sealed with aluminium caps. The vials are sterilized with moist heat.

As can be seen from the table below, the formulation is stable even after severe heat intake of 121° C./60 minutes

| Test | prior to sterilization | after sterilization (121° C./60 min effective dwel time) |
|---|---|---|
| Color | colorless | colorless |
| Clarity | clear, particle free | clear, particle free |
| pH-value | 6.3 | 6.1 |

No change in assay value is observed, and prior as well as after sterilization no degradation products at levels above the limit of detection could be found.

Example 9

Zoledronic Acid 5 mg/100 mL

| Ingredient | Amount [g] per 1 L |
|---|---|
| Zoledronic acid monohydrate Corresponding to 0.0500 g zoledronic acid anhydrous | 0.0533 g |
| Glycerol water free | 22.5 g |
| Sodium citrate | 0.300 g |
| Water for injection | Up to 1.00 L |

Approx. 800 g of water for injection are filled into the compounding vessel. The excipients glycerol and sodium citrate are added and dissolved under stirring. The drug substance zoledronic acid is added and dissolved under stirring. The preparation is adjusted to the final volume with water for injection. The solution is filtered into the vials through a filter of 0.2 μm pore size. Washed and dried Daikyo CZ plastic vials are filled with the bulk solution. Sterilized Helvoet FM259/0 Omniflex plus coated stoppers are inserted into the vials, and the stoppered vials are sealed with aluminium caps. The vials are sterilized with moist heat.

As can be seen from the table below, the formulation is stable even after severe heat intake of 121° C./60 minutes

| Test | prior to sterilization | after sterilization (121° C./60 min effective dwell time) |
|---|---|---|
| Color | colorless | colorless |
| Clarity | clear, particle free | clear, particle free |
| pH-value | 6.4 | 6.2 |

No change in assay value is observed, and prior as well as after sterilization no degradation products at levels above the limit of detection could be found.

Example 10

Zoledronic Acid 5 mg/100 mL

| Ingredient | Amount [g] per 1 L |
|---|---|
| Zoledronic acid monohydrate Corresponding to 0.0500 g zoledronic acid anhydrous | 0.0533 g |
| 1,2 propylene glycol | 19.0 g |
| Sodium citrate | 0.300 g |
| Water for injection | Up to 1.00 L |

Approx. 800 g of water for injection are filled into the compounding vessel. The excipients Propylene glycol and sodium citrate are added and dissolved under stirring. The drug substance zoledronic acid is added and dissolved under stirring. The preparation is adjusted to the final volume with water for injection. The solution is filtered into the vials through a filter of 0.2 μm pore size. Washed and dried Daikyo CZ plastic vials are filled with the bulk solution. Sterilized Helvoet FM259/0 Omniflex plus coated stoppers are inserted into the vials, and the stoppered vials are sealed with aluminium caps. The vials are sterilized with moist heat.

As can be seen from the table below, the formulation is stable even after severe heat intake of 121° C./60 minutes

| Test | prior to sterilization | after sterilization (121° C./60 min effective dwell time) |
|---|---|---|
| Color | colorless | colorless |
| Clarity | clear, particle free | clear, particle free |
| pH-value | 6.4 | 6.3 |

No change in assay value is observed, and prior as well as after sterilization no degradation products at levels above the limit of detection could be found.

Example 11

Washing of Vials/Endotoxin Removal

The plastic vials are processed on a conventional integrated automatic liquid filling processing line. Washing is performed in a conventional rotary vial washing machine (e.g. Bausch&Stroebel FAU 6000 or Bosch RRU 2020) as used for glass vials. The vials are put on the feeding belt of the washing machine. In a first instance the vials are submerged in a bath with hot water and treated by sonication. After that the vials are transported to the rotary washing station and are inverted. Cleaning is accomplished by a programmed process of air and water flushing through nozzles inserted into the vials. The vials are first washed with recycled hot Water for Injections (>70° C.), blown out with filtered air, then washed again with fresh hot Water for Injections and blown out with filtered air. Following washing, the vials are inverted again to their normal position, and then transferred by the conveyor to the belt of the hot air tunnel, where they are dried at 110° C. On a Bausch&Stroebel FAU 6000 washing machine, a washing speed of 84 vials/min is suitable.

On a Bosch RRU 2020, a suitable washing speed is at a machine setting of 5.8-6.5 scale units.

The efficiency of this process has been assessed by comparison of the endotoxin load of endotoxin-spiked vials prior and after the routine washing process. The results show more than 3 log reduction of the endotoxin challenge, i.e. the requirement of more than a 3 log reduction was met at each position tested during the washing process.

Endotoxin Recovery from Treated Vials

Endotoxin is spiked into the plastic vials and dried. The endotoxin spike recovery from five non washed vials is determined in duplicate (spike controls). The spike is 8538 EU (IU) per vial, i.e. the mean value of the results minus two times the standard deviation.

Three qualification runs are performed. In each run 10 vials spiked with endotoxin are distributed into one batch of un-spiked vials and are washed in the washing machine.
Results of Endotoxin Recovery:

|  | EU (IU)/vial | | |
| --- | --- | --- | --- |
|  | Run 1 | Run 2 | Run 3 |
| Vial 1 | <0.63 | <0.63 | 1.57 |
| Vial 2 | <0.63 | <0.63 | <0.63 |
| Vial 3 | <0.63 | <0.63 | <0.63 |
| Vial 4 | 0.64 | <0.63 | <0.63 |
| Vial 5 | <0.63 | <0.63 | <0.63 |

-continued

|  | EU (IU)/vial | | |
| --- | --- | --- | --- |
|  | Run 1 | Run 2 | Run 3 |
| Vial 6 | <0.63 | <0.63 | <0.63 |
| Vial 7 | <0.63 | <0.63 | <0.63 |
| Vial 8 | <0.63 | <0.63 | <0.63 |
| Vial 9 | <0.63 | <0.63 | <0.63 |
| Vial 10 | <0.63 | <0.63 | <0.63 |

In all vials tested an endotoxin reduction of at least a factor 1000 is shown.

Example 12

Sterilization of Zoledronic Acid 5 mg/100 mL

Studies have shown that the solution for infusion is chemically and physically stable during autoclaving. Upon sterilisation of up to 150 minutes at $\geq 121°$ C. no degradation of the drug substance could be observed (please see results in the table below). This heat resistance allows an overkill sterilisation cycle yielding a sterility assurance level (SAL) of at least $10^{-12}$.

Based on the spore reduction kinetics, expressed in the decimal reduction value (D-value) of *Geobacillus stearothermophilus* spores in the Zoledronic acid 5 mg/100 mL drug product solution, a sterilisation time (dwell time) of 30 minutes was derived to obtain the desired spore reduction rate. The chosen sterilization procedure is in line with the requirements of Ph. Bur. and USP.

| Stability of Zoledronic acid 5 mg/100 ml upon prolonged sterilization times | | | |
| --- | --- | --- | --- |
| Parameter | Autoclaved 30 minutes/121° C. | Autoclaved for additional 60 min/124° C. | Autoclaved for additional 2 times 60 min/124° C. |
| Overall dwell time at >121° C. | 30 min. | 90 min. | 150 min. |
| Appearance of the container | 100 ml colourless plastic vials, grey rubber-stopper, aluminium cap with plastic flip component | 100 ml colourless plastic vials, grey rubber-stopper, aluminium cap with plastic flip component | 100 ml colourless plastic vials, grey rubber-stopper, aluminium cap with plastic flip component |
| Appearance of the solution | clear, colourless solution | clear, colourless solution | clear, colourless solution |
| Absorbance of the solution* | 0.00 | 0.00 | 0.00 |
| pH value | 6.6 | 6.6 | 6.6 |
| Particulate matter: | | | |
| >25 μm | 0 (USP) 3 (Ph. Eur.) | 0 (USP) 0 (Ph. Eur.) | 0 (USP) 7 (Ph. Eur.) |
| >10 μm | 20 (USP) 13 (Ph. Eur). | 10 (USP) 3 (Ph. Eur). | 0 (USP) 10 (Ph. Eur). |
| Degradation products | <0.1% | <0.1% | <0.1% |
| Assay of zoledronic acid | 98.7% | 99.6% | 99.3% |
| Bacterial endotoxins | <0.025 EU (IU)/mL | <0.025 EU (IU)/mL | <0.025 EU (IU)/mL |
| Container/closure tightness by dye intrusion | Complies: no unit out of 40 vials tested shows sign for dye ingress | Complies: no unit out of 40 vials tested shows sign for dye ingress | Complies: no unit out of 40 vials tested shows sign for dye ingress |

Compared to multiple sterilization in glass vials, no increase in particulate matter is detected. The formulation is stable even after a total sterilization time of 150 minutes at >121° C.

Example 13

Evaluation of Plastic Vials Under Worst Case Sterilization Conditions

During processing, the vials are exposed to dry heat (drying after washing) of up to 120° C. and moist heat (during autoclaving) of up to 124° C. To assess any potential risk for damage of the vial and the container closure integrity, a heat resistance study has been performed.

20 empty vials as used for Example 2 are subjected to dry heat at 125° C. for 10 hours, which is above the temperature of a drying process which is normally set to 100-120° C. Prior and after heat treatment the inner diameter and the ovality of the vial neck were determined as these dimensions are considered to be the most critical parameters for vial tightness. A negligible reduction of the inner diameter of the vial neck by 0.03 mm (range 0.02-0.05 mm) is observed. The apparent ovality, given as the difference of two perpendicular diameters of the vial opening divided by the sum of these diameters, remained unchanged and is 0.18% in the selected samples (prior to treatment: range 0.05-0.45%; after treatment: range 0.00-0.50%).

Vials from Example 2 are subjected to a worst case steam sterilization cycle of 60 minutes in saturated steam at 124.5° C., which is above the thermal deformation temperature of the vial of 123° C. according to ASTM D648). Supporting overpressure is not applied during the sterilisation phase. Sterilized as well as not-sterilized reference samples are tested for dimensional changes as well as for tightness by dye intrusion and weight loss.

Results of the evaluation of vials in worst case sterilization

|  | Before sterilization | After sterilization (124.5° C./60 min) |
|---|---|---|
| Weight loss (2 weeks, 40° C.), n = 20 | 21 mg (range: 20-22 mm) | 22 mg (range: 21-23 mm) |
| Inner diameter of vial mouth, n = 20 | 22.0 mm (range: 21.96-22.04 mm) | 22.1 mm (range: 22.09-22.18 mm) |
| Apparent ovality of inner diameter of vial mouth, n = 8 | 0.11% (range: 0.00-0.23%) | 0.20% (range: 0.00-0.41%) |
| Container closure tightness by dye intrusion, n = 40 | tight | tight |

Sterilization at worst case conditions does not have any detectable influence on vial tightness as expressed by weight loss and resistance to dye intrusion. A very slight change is observed in the inner diameter of the vial mouth, but the values are within the specifications of 22.0+/−0.2 mm.

Example 14

Analytics of Zoledronic Acid 4 mg/100 mL Solutions

| | |
|---|---|
| Column | Luna, RP-C18 (2), 5 μm (in steel), Phenomenex Length 250 mm, internal diameter 4.6 mm, or equivalent column |
| Stock solution EDTA | Accurately weigh to 0.001 g 0.365 g of EDTA into a 100 ml volumetric flask, dissolve with 5 ml 2 M NaOH and fill up to the mark with water |
| Mobile phase | Accurately weigh to 0.1 g 6.2 g of disodium hydrogen phosphate dihydrate (35 mM) and 4.5 g of tetrahexyl-ammonium hydrogen sulfate (10 mM) into a flask, add 900 ml of water, 100 ml of acetonitrile dissolve and add 2 ml of EDTA stock solution and mix thoroughly. Adjust the pH to 7.9 with 2 M sodium hydroxide solution. |
| Flow rate | 1.2 ml/min |
| Detection | 215 nm |
| Temperature | 30° C. |
| Injection volume | 160 μl |
| Run time | Approx. 80 min |
| Important remarks | PEEK capillaries are recommended at least between column and detector In order to avoid adsorption on glass surfaces use plastic auto sampler vials and pasteur pipettes made from plastic. Reference solutions have to be prepared with volumetric flasks of frequently used glassware or of plastic and stored in plastic flasks. |

Example 15

Ready-to Use Formulations of Pamidronic Acid

| | Composition per unit dose pack of 100.0 mL equivalent to 101.5 g: | | | |
|---|---|---|---|---|
| Ingredient | 15 mg/100 mL strength | 30 mg/100 mL strength | 60 mg/100 mL strength | 90 mg/100 mL strength |
| Pamidronic acid disodium salt pentahydrate | 19.79 mg | 39.58 mg | 79.16 mg | 118.74 mg |

-continued

| | Composition per unit dose pack of 100.0 mL equivalent to 101.5 g: | | | |
|---|---|---|---|---|
| Ingredient | 15 mg/100 mL strength | 30 mg/100 mL strength | 60 mg/100 mL strength | 90 mg/100 mL strength |
| equivalent to pamidronic acid | 15 mg | 30 mg | 60 mg | 90 mg |
| Citric acid Ph. Eur. up to pH 6.5 | approx. 1.5 mg | approx. 3 mg | approx. 6 mg | approx. 9 mg |
| Mannitol Ph. Eur. | 5185 mg | 5170 mg | 5140 mg | 5110 mg |
| Water for injection | 96.29 g | 96.28 g | 96.27 g | 96.26 g |

Based on the basic composition of one dosage form unit given in the table above, the amount needed for the batch to be manufactured is calculated. A typical batch size is approx. 5 L for a lab scale batch, 100 L for a pilot scale batch and 1000 L for a production scale batch.

Approx. 85-95% of the total amount of water for injection are filled into a stainless steel compounding vessel. Mannitol is added and dissolved under stirring. The drug substance pamidrionic acid disodium salt pentahydrate is added and dissolved under stirring. The pH value is adjusted with a 5% solution of citric acid in water for injection. The preparation is adjusted to the final weigh with water for injection. The bulk solution is passed to the filling line and filter in-line through a filter of 0.2 µm pore size. Washed and dried Daikyo CZ 100 mL plastic vials are filled with each 102 mL of the bulk solution. Sterilized Helvoet FM259/0 Omniflex plus coated stoppers are inserted into the vials, and the stoppered vials are sealed with aluminium caps. The vials are sterilized with moist heat at >121° C. for at least 15 minutes (effective dwell time).

Example 16

Ready-to Use Formulations of Pamidronic Acid

| | Composition per unit dose pack of 100.0 mL equivalent to 101.5 g: | | | |
|---|---|---|---|---|
| Ingredient | 15 mg/100 mL strength | 30 mg/100 mL strength | 60 mg/100 mL strength | 90 mg/100 mL strength |
| Pamidronic acid disodium salt pentahydrate | 19.79 mg | 39.58 mg | 79.16 mg | 118.74 mg |
| equivalent to pamidronic acid | 15 mg | 30 mg | 60 mg | 90 mg |
| Phosphoric acid 85% up to pH 6.3 | approx. 2.35 mg | approx. 4.7 mg | approx. 9.4 mg | approx. 14.1 mg |
| Mannitol Ph. Eur. | 5185 mg | 5170 mg | 5140 mg | 5110 mg |
| Water for injection | 96.29 g | 96.28 g | 96.27 g | 96.26 g |

Based on the basic composition of one dosage form unit given in the table above, the amount needed for the batch to be manufactured is calculated. A typical batch size is approx. 5 L for a lab scale batch, 100 L for a pilot scale batch and 1000 L for a product-ion scale batch.

Approx. 85-95% of the total amount of water for injection are filled into a stainless steel compounding vessel. Mannitol is added and dissolved under stirring. The drug substance pamidrionic acid disodium salt pentahydrate is added and dissolved under stirring. The pH value of pH 6.3 is adjusted with a 5% solution of phosphoric acid in water for injection. The preparation is adjusted to the final weight with water for injection. The bulk solution is passed to the filling line and filter in-line through a filter of 0.2 µm pore size. Washed and dried Daikyo CZ 100 mL plastic vials are filled with each 102 mL of the bulk solution. Sterilized Helvoet FM259/0 Omniflex plus coated stoppers are inserted into the vials, and the stoppered vials are sealed with aluminium caps. The vials are sterilized with moist heat at >121° C. for at least 15 minutes (effective dwell time).

Example 17

Ready-to Use Formulations of Pamidronic Acid

| Composition per unit dose pack of 100.0 mL equivalent to 101.5 g: | | | | |
|---|---|---|---|---|
| Ingredient | 15 mg/100 mL strength | 30 mg/100 mL strength | 60 mg/100 mL strength | 90 mg/100 mL strength |
| Pamidronic acid disodium salt pentahydrate | 19.79 mg | 39.58 mg | 79.16 mg | 118.74 mg |
| equivalent to pamidronic acid | 15 mg | 30 mg | 60 mg | 90 mg |
| Acetic acid glacial Ph. Eur. up to pH 6.5 | approx. 1.25 mg | approx. 2.5 mg | approx. 5.0 mg | approx. 7.5 mg |
| Mannitol Ph. Eur. | 5185 mg | 5170 mg | 5140 mg | 5110 mg |
| Water for injection | 96.29 g | 96.28 g | 96.27 g | 96.26 g |

Based on the basic composition of one dosage form unit given in the table above, the amount needed for the batch to be manufactured is calculated. A typical batch size is approx. 5 L for a lab scale batch, 100 L for a pilot scale batch and 1000 L for a production scale batch.

Approx. 85-95% of the total amount of water for injection are filled into a stainless steel compounding vessel. Mannitol is added and dissolved under stirring. The drug substance pamidrionic acid disodium salt pentahydrate is added and dissolved under stirring. The pH value of pH 6.3 is adjusted with a 5% solution of acetic acid in water for injection. The preparation is adjusted to the final weight with water for injection. The bulk solution is passed to the filling line and filter in-line through a filter of 0.2 μm pore size. Washed and dried Daikyo CZ 100 mL plastic vials are filled with each 102 mL of the bulk solution. Sterilized Helvoet FM259/0 Omniflex plus coated stoppers are inserted into the vials, and the stoppered vials are sealed with aluminium caps. The vials are sterilized with moist heat at >121° C. for at least 15 minutes (effective dwell time).

Example 18

Ready-to Use Formulations of Pamidronic Acid

| Composition per unit dose pack of 100.0 mL equivalent to 101.5 g: | | | | |
|---|---|---|---|---|
| Ingredient | 15 mg/100 mL strength | 30 mg/100 mL strength | 60 mg/100 mL strength | 90 mg/100 mL strength |
| Pamidronic acid disodium salt pentahydrate | 19.79 mg | 39.58 mg | 79.16 mg | 118.74 mg |
| equivalent to pamidronic acid | 15 mg | 30 mg | 60 mg | 90 mg |
| Lactic acid Ph. Eur. up to pH 6.5 | approx. 2.5 mg | approx. 5.0 mg | approx. 10.0 mg | approx. 15.0 mg |
| Mannitol Ph. Eur. | 5185 mg | 5170 mg | 5140 mg | 5110 mg |
| Water for injection | 96.29 g | 96.28 g | 96.27 g | 96.26 g |

Based on the basic composition of one dosage form unit given in the table above, the amount needed for the batch to be manufactured is calculated. A typical batch size is approx. 5 L for a lab scale batch, 100 L for a pilot scale batch and 1000 L for a production scale batch.

Approx. 85-95% of the total amount of water for injection are filled into a stainless steel compounding vessel. Mannitol is added and dissolved under stirring. The drug substance pamidrionic acid disodium salt pentahydrate is added and dissolved under stirring. The pH value of pH 6.3 is adjusted with a 5% solution of lactic acid in water for injection. The preparation is adjusted to the final weight with water for injection. The bulk solution is passed to the filling line and filter in-line through a filter of 0.2 μm pore size. Washed and dried Daikyo CZ 100 mL plastic vials are filled with each 102 mL of the bulk solution. Sterilized Helvoet FM259/0 Omniflex plus coated stoppers are inserted into the vials, and the stoppered vials are sealed with aluminium caps. The vials are sterilized with moist heat at >121° C. for at least 15 minutes (effective dwell time).

Example 19

Ready-to Use Formulations of Pamidronic Acid

| Ingredient | Composition per unit dose pack of 100.0 mL equivalent to 101.5 g: | | | |
|---|---|---|---|---|
| | 15 mg/100 mL strength | 30 mg/100 mL strength | 60 mg/100 mL strength | 90 mg/100 mL strength |
| Pamidronic acid disodium salt pentahydrate | 19.79 mg | 39.58 mg | 79.16 mg | 118.74 mg |
| equivalent to pamidronic acid | 15 mg | 30 mg | 60 mg | 90 mg |
| Tartaric acid Ph. Eur. up to pH 6.5 | approx. 1.5 mg | approx. 3.0 mg | approx. 6.0 mg | approx. 9.0 mg |
| Mannitol Ph. Eur. | 5185 mg | 5170 mg | 5140 mg | 5110 mg |
| Water for injection | 96.29 g | 96.28 g | 96.27 g | 96.26 g |

Based on the basic composition of one dosage form unit given in the table above, the amount needed for the batch to be manufactured is calculated. A typical batch size is approx. 5 L for a lab scale batch, 100 L for a pilot scale batch and 1000 L for a production scale batch.

Approx. 85-95% of the total amount of water for injection are filled into a stainless steel compounding vessel. Mannitol is added and dissolved under stirring. The drug substance pamidronic acid disodium salt pentahydrate is added and dissolved under stirring. The pH value of pH 6.3 is adjusted with a 5% solution of tartaric acid in water for injection. The preparation is adjusted to the final weight with water for injection. The bulk solution is passed to the filling line and filter in-line through a filter of 0.2 μm pore size. Washed and dried Daikyo CZ 100 mL plastic vials are filled with each 102 mL of the bulk solution. Sterilized Helvoet FM259/0 Omniflex plus coated stoppers are inserted into the vials, and the stoppered vials are sealed with aluminium caps. The vials are sterilized with moist heat at >121° C. for at least 15 minutes (effective dwell time).

The invention claimed is:

1. A pharmaceutical product comprising
   a) a heat sterilizable container having an internal surface that comprises a plastic material; and
   b) a ready to use solution disposed in the container, said solution comprising 2-(imidazol-1yl)-1-hydroxyethane-1,1-diphosphonic acid (zoledronic acid) or a pharmacologically acceptable salt thereof,
   wherein the product is in unit dose form having a volume of from about 20 ml up to about 500 ml.

2. The product according to claim 1, wherein the solution further comprises a buffering agent.

3. The product according to claim 2, wherein the buffering agent comprises an organic base and wherein the solution is adjusted with the organic base to a physiologically acceptable pH value of pH 5.5-8.0.

4. The product according to claim 3, wherein the organic base is sodium citrate.

5. The product according to claim 3, wherein the organic base is sodium acetate.

6. The product according to claim 2, wherein the buffering agent is sodium or potassium phosphate.

7. The product according to claim 2, wherein the buffering agent is sodium or potassium hydroxide.

8. The product according to claim 1, wherein the solution further comprises an isotonizing agent.

9. The product according to claim 8, wherein the isotonizing agent is a non-ionic isotonizing agent in which the solution is analyzable with a limit of quantitation for the concentration of the zoledronic acid or the pharmacologically acceptable salt thereof and byproducts and degradation products of the zoledronic acid or the pharmacologically acceptable salt thereof of at least 0.1% related to a declared dose.

10. The product according to claim 9, wherein the solution is analyzable by reversed phase chromatography with a complexation agent for determination of the concentration of the zoledronic acid or the pharmacologically acceptable salt thereof and byproducts and degradation products of the zoledronic acid or the pharmacologically acceptable salt thereof.

11. A pharmaceutical product comprising,
   a) a terminally heat sterilizable container having an internal surface that comprises a plastic material, and
   b) a ready to use solution disposed in the container, said solution comprising
      i. a unit dose of zoledronic acid or a pharmacologically acceptable salt thereof;
      ii. an organic base buffering agent, and
      iii. a non-ionic isotonizing agent.

12. The product according to claim 1, wherein the container is a prefillable plastic syringe.

13. The product according to claim 1, wherein the plastic material is transparent.

14. The product according to claim 1, wherein the plastic material is a cycloolefinic polymer.

15. The product according to claim 14, wherein the plastic material is a Daikyo CZ resin.

16. The product according to claim 1, wherein the container is an infusion bag.

17. The product according to claim 16, wherein the infusion bag is made of polypropylene or a polypropylene/Kraton blend, or wherein the infusion bag is a multilayer bag having polypropylene or polyethylene on the internal surface.

18. The product according to claim 1, wherein the container is made by the Blow/Fill/Seal technology, and further wherein the container is made of polyethylene or polypropylene.

19. The product according to claim 18, wherein the container is made of polypropylene.

20. The product according to claim 18, wherein the container is made of Rexene 32M2 polypropylene.

21. A process for the production of a ready to use pharmaceutical product comprising,
   a) filling a container having an internal surface with a solution comprising a zoledronic acid or a pharmacologically acceptable salt thereof, wherein the internal surface of the container comprises a transparent plastic material; and
   b) sterilizing the container.

22. The process according to claim 21, wherein step b) is achieved by terminal heat sterilization.

23. The process according to claim 22, wherein heat sterilization is at a temperature of at least about 110° C. or higher.

24. The process according to claim 21, wherein step b) occurs from about 15 minutes up to about 3 hours.

25. The process according to claim 22, wherein heat sterilization is achieved by autoclaving conditions applied to obtain a sterility assurance level of at least $10^{-6}$.

26. The process according to claim 22, wherein heat sterilization is achieved by autoclaving conditions applied to obtain a sterility assurance level of at least $10^{-12}$.

27. The process according to claim 21, wherein the container is depyrogenised before filling with the solution.

28. The process according to claim 21, wherein the container is an endotoxin/pyrogen-free or a substantially endotoxin/pyrogen-free container.

29. The process according to claim 21, wherein the solution further comprises a non-ionic isotonizing agent and wherein the process further comprises the step of determining the concentration of the zoledronic acid or the pharmacologically acceptable salt thereof and byproducts and degradation products of the zoledronic acid or the pharmacologically acceptable salt thereof, wherein said determining step is achieved by ion chromatography, capillary electrophoresis, or high performance liquid chromatography (HPLC).

30. The process according to claim 19, wherein the solution further comprises a non-ionic isotonizing agent and wherein the process further comprises the step of determining the concentration of the zoledronic acid or the pharmacologically acceptable salt thereof and byproducts and degradation products of the zoledronic acid or the pharmacologically acceptable salt thereof, wherein said determining step is achieved by reversed phase chromatography with a complexation agent.

* * * * *